United States Patent
Manak et al.

(10) Patent No.: US 10,098,603 B2
(45) Date of Patent: Oct. 16, 2018

(54) METHOD FOR ESTIMATION AND CORRECTION OF GRID PATTERN DUE TO SCATTER

(71) Applicant: Toshiba Medical Systems Corporation, Otawara-shi (JP)

(72) Inventors: Joseph Manak, Albany, NY (US); Amit Jain, Amherst, NY (US); Hisato Takemoto, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 53 days.

(21) Appl. No.: 15/099,720

(22) Filed: Apr. 15, 2016

(65) Prior Publication Data
US 2017/0296132 A1    Oct. 19, 2017

(51) Int. Cl.
*A61B 6/03* (2006.01)
*G06T 7/00* (2017.01)
(Continued)

(52) U.S. Cl.
CPC .......... *A61B 6/5282* (2013.01); *A61B 6/5211* (2013.01); *A61B 6/5258* (2013.01);
(Continued)

(58) Field of Classification Search
CPC ......... A61B 6/00; A61B 6/4291; A61B 6/488; A61B 6/52; A61B 6/5205; A61B 6/5211;
(Continued)

(56) References Cited

U.S. PATENT DOCUMENTS 6,460,003 B1 * 10/2002 Kump .................... A61B 6/583
    382/128
7,147,372 B2 * 12/2006 Nelson ................. A61B 6/4233
    378/207

(Continued)

FOREIGN PATENT DOCUMENTS

JP    3277866    2/2002
JP    3698167    7/2005

OTHER PUBLICATIONS

Seibert, J.A., et al., "Scatter Removal in Digital X-ray Images by Combined Monte Carlo and Analytical Techniques", (1989), SPIE Medical Imaging III: Image Processing, vol. 1092, pp. 356-366.*

*Primary Examiner* — Anastasia Midkiff
(74) *Attorney, Agent, or Firm* — Oblon, McClelland, Maier & Neustadt, L.L.P.

(57) ABSTRACT

An apparatus for generating corrected X-ray projection data from target X-ray projection data obtained by performing an X-ray scan with a detector having an anti-scatter grid, and a method for creating a lookup table and generating corrected X-ray projection data. The apparatus includes a detector configured to detect incident X-rays, an anti-scatter grid configured to suppress scattered radiation incident on the detector, and an X-ray source configured to irradiate the target with X-rays. Processing circuitry is configured to cause the X-ray source to scan, using a peak kilovoltage (kVp), the target to produce the target projection data, determine a patient-to-detector distance (PDD) and an area irradiated (FS), transform the target projection data into a spatial frequency domain, determine scatter values by accessing the lookup table using the kVp, PDD, and FS values, and subtract the scatter values from the frequency components to obtain the corrected X-ray projection data.

20 Claims, 9 Drawing Sheets

(51) Int. Cl.
   *G06T 11/00*   (2006.01)
   *A61B 6/00*    (2006.01)
   *G01T 7/00*    (2006.01)
   *G06T 5/50*    (2006.01)

(52) U.S. Cl.
   CPC .............. *A61B 6/583* (2013.01); *A61B 6/585* (2013.01); *G01T 7/005* (2013.01); *G06T 7/0014* (2013.01); *G06T 11/005* (2013.01); *A61B 6/488* (2013.01); *A61B 2560/0228* (2013.01); *G01N 2223/051* (2013.01); *G06T 5/50* (2013.01)

(58) Field of Classification Search
   CPC . A61B 6/5252; A61B 6/5258; A61B 6/52582; A61B 6/5294; A61B 6/58; A61B 6/583; A61B 6/585; A61B 2560/00; A61B 2560/02; A61B 2560/0223; A61B 2560/0228; A61B 2560/0238; G06T 1/00; G06T 1/0007; G06T 1/60; G06T 5/00; G06T 5/001; G06T 5/006; G06T 5/50; G06T 7/00; G06T 7/0002; G06T 7/0012; G06T 7/0014; G06T 7/10; G06T 7/168; G06T 7/174; G06T 9/00; G06T 9/007; G06T 11/00; G06T 11/003; G06T 11/005; G06T 2207/00; G06T 2207/10; G06T 2207/10072; G06T 2207/10081; G06T 2207/10116; G06T 2207/10121; G06T 2207/20; G06T 2207/20036; G06T 2207/20041; G06T 2207/20048; G06T 2207/20056; G06T 2207/20175; G06T 2207/20185; G06T 2207/20212; G06T 2207/20216; G06T 2207/20224; G01T 1/00; G01T 1/29; G01T 1/2914; G01T 7/005; G01N 2223/00; G01N 2223/05; G01N 2223/051; G01N 2223/40; G01N 2223/401; G21K 1/00; G21K 1/02; G21K 1/025

See application file for complete search history.

(56) References Cited

U.S. PATENT DOCUMENTS

| | | | |
|---|---|---|---|
| 7,480,363 B2 * | 1/2009 | Lasiuk | G01B 15/025 378/54 |
| 8,043,003 B2 | 10/2011 | Vogt et al. | |
| 2002/0080909 A1 | 6/2002 | Op De Beek et al. | |
| 2008/0056445 A1 * | 3/2008 | Spahn | A61B 6/544 378/62 |
| 2012/0148156 A1 * | 6/2012 | Sehnert | A61B 6/4291 382/171 |
| 2015/0173703 A1 | 6/2015 | Siewerdsen et al. | |

* cited by examiner

METHOD FOR ESTIMATION AND CORRECTION OF GRID PATTERN DUE TO SCATTER

BACKGROUND

Field

This disclosure is related to computed tomography (CT) image reconstruction of projection data obtain using a CT scanner, and more particularly relates to estimating and reducing image artifacts due to anti-scatter grids.

Discussion of the Background

Computed tomography (CT) systems and methods are widely used, particularly for medical imaging and diagnosis. CT systems generally create images of one or more sectional slices through a subject's body. A radiation source, such as an X-ray source, irradiates the body from one side. A collimator, generally adjacent to the X-ray source, limits the angular extent of the X-ray beam, so that radiation impinging on the body is substantially confined to a cone-beam/fan-beam region (i.e., an X-ray projection volume) defining an image volume of the body. At least one detector (and generally many more than one detector) on the opposite side of the body receives radiation transmitted through the body substantially in the projection volume. The attenuation of the radiation that has passed through the body is measured by processing electrical signals received from the detector.

In general, an X-ray projection image contains many scattered radiation components. This scattered radiation greatly degrades the accuracy of a CT value in three-dimensional imaging using a two-dimensional detector. An X-ray beam in the presence of a scattering object can be modeled as a primary X-ray beam P(x, y) and a scattered X-ray beam S(x, y), wherein the projection data T(x, y) is a composite of these two:

$$T(x,y)=P(x,y)+S(x,y).$$

A two-dimensional detector, like a flat-panel detector used in an X-ray diagnostic apparatus, uses a scattered-radiation-removing grid, called an anti-scatter grid, to suppress scattered radiation.

The anti-scatter grid, in addition to suppressing scattered radiation, is itself also imaged by the two-dimensional detector. A conventional technique to remove the anti-scatter grid from the image uses dark images, which are images taken while the detector is not illuminated by the X-ray source, and flat-field images, which are images taken without a target and with uniform illumination by the X-ray source, to correct the two-dimensional image for the presence of the anti-scatter grid.

However, this technique does not completely correct the grid pattern in an actual image. Further, this problem appears in many fields related to computed tomography that use an anti-scatter grid over a detector, such as conventional X-ray, conventional CT, single-photon emission CT (SPECT), positron emission tomography (PET), fluoroscopy, angiography, and the like, and appears whether the anti-scatter grid and detector are one- or two-dimensional.

BRIEF DESCRIPTION OF THE DRAWINGS

A more complete appreciation of the disclosed embodiments and many of the attendant advantages thereof will be more readily obtained by reference to the accompanying drawings when considered in connection with following detailed description, wherein.

DETAILED DESCRIPTION

The following descriptions are meant to further clarify the present disclosure by giving specific examples and embodiments of the disclosure. These embodiments are meant to be illustrative rather than exhaustive. The full scope of the disclosure is not limited to any particular embodiment disclosed in this specification, but rather is defined by the claims.

Figure 1:
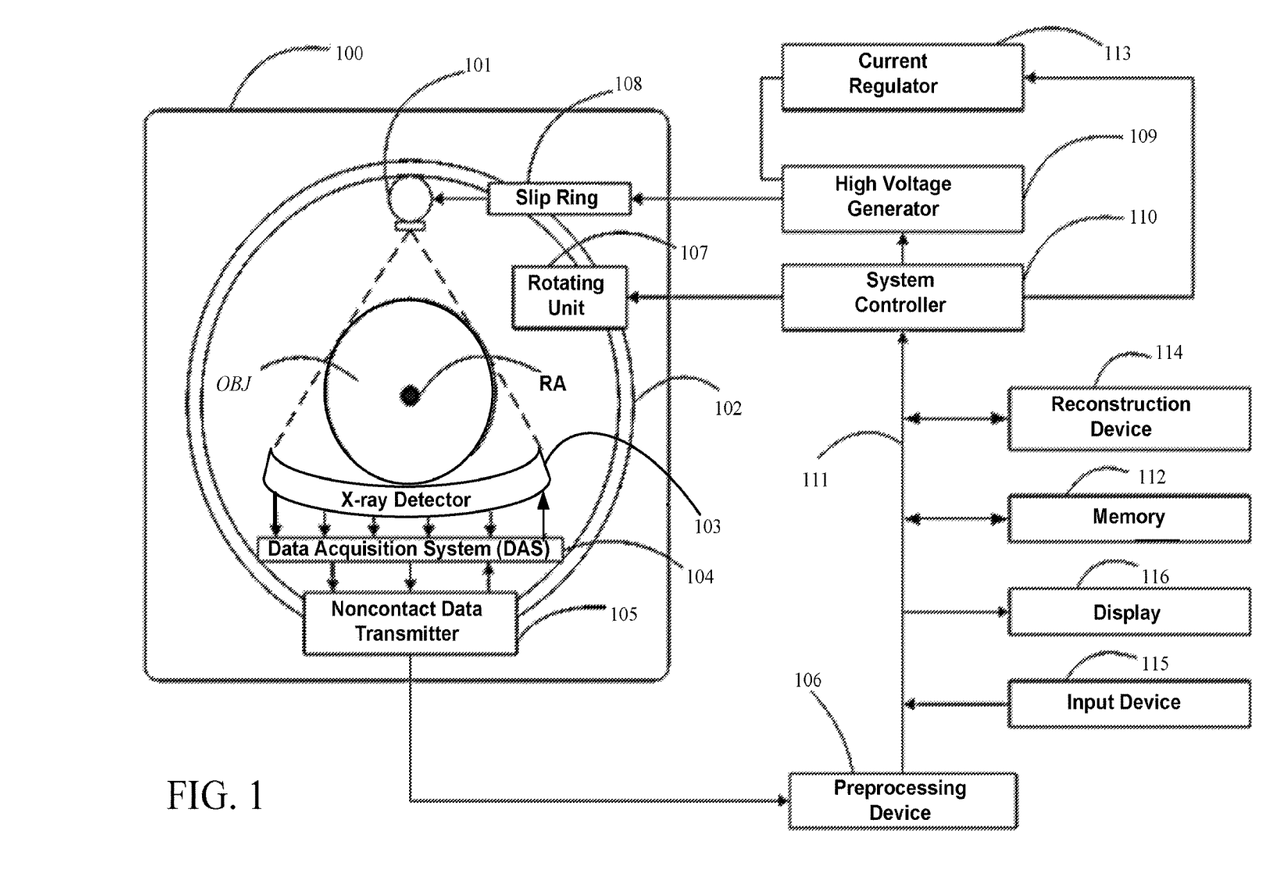
FIG. 1 illustrates a schematic of an implementation of a computed tomography scanner.

Referring now to the drawings, wherein like reference numerals designate identical or corresponding parts throughout the several views, FIG. 1 illustrates an implementation of the radiography gantry included in a CT apparatus or scanner. As shown in FIG. 1, a radiography gantry 100 is illustrated from a side view and further includes an X-ray tube 101, an annular frame 102, and a multi-row or two-dimensional-array-type X-ray detector 103. The X-ray tube 101 and X-ray detector 103 are diametrically mounted across an object OBJ on the annular frame 102, which is rotatably supported around a rotation axis RA. A rotating unit 107 rotates the annular frame 102 at a high speed, such as 0.4 sec/rotation, while the object OBJ is being moved along the axis RA into or out of the illustrated page.

The first embodiment of an X-ray computed tomography apparatus according to the present inventions will be described below with reference to the views of the accompanying drawing. Note that X-ray computed tomography apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate type, which is currently the mainstream, will be exemplified.

The X-ray CT apparatus further includes a high voltage generator 109 that generates a tube voltage applied to the X-ray tube 101 through a slip ring 108 so that the X-ray tube 101 generates X-rays. The X-rays are emitted towards the object OBJ, whose cross-sectional area is represented by a circle. The X-ray detector 103 is located at an opposite side from the X-ray tube 101 across the object OBJ for detecting the emitted X-rays that have transmitted through the object OBJ. The X-ray detector 103 further includes individual detector elements or units.

The CT apparatus further includes other devices for processing the detected signals from X-ray detector 103. A data acquisition circuit or a Data Acquisition System (DAS) 104 converts a signal output from the X-ray detector 103 for each channel into a voltage signal, amplifies the signal, and further converts the signal into a digital signal. The X-ray detector 103 and the DAS 104 are configured to handle a predetermined total number of projections per rotation (TPPR). Examples of TPPRs include, but are not limited to 900 TPPR, 900-1800 TPPR, and 900-3600 TPPR.

The above-described data is sent to a preprocessing device 106, which is housed in a console outside the radiography gantry 100 through a non-contact data transmitter 105. The preprocessing device 106 performs certain corrections, such as sensitivity correction on the raw data. A memory 112 stores the resultant data, which is also called projection data, at a stage immediately before reconstruction processing. The memory 112 is connected to a system controller 110 through a data/control bus 111, together with a reconstruction device 114, input device 115, and display 116. The system controller 110 controls a current regulator 113 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 101 and the X-ray detector 103 are diametrically mounted on the annular frame 102 and are rotated around the object OBJ as the annular frame 102 is rotated about the rotation axis RA. In the fourth-generation geometry system, the detectors are fixedly placed around the patient and an X-ray tube rotates around the patient. In an alternative embodiment, the radiography gantry 100 has multiple detectors arranged on the annular frame 102, which is supported by a C-arm and a stand.

In what follows, a detailed description of the embodiments used to reduce imaging artifacts due to anti-scatter grids in CT is provided. In addition to conventional CT, the embodiments described herein are also applicable to a fourth-generation CT system, a third-generation CT system, and/or a combination of third- and fourth-generation CT systems.

The memory 112 can store the measurement value representative of the irradiance of the X-rays at the X-ray detector 103. Further, the memory 112 can store a dedicated program for executing the CT image reconstruction methods.

The reconstruction device 114 can execute the CT image reconstruction methods, and perform estimation and correction of grid pattern due to scatter. Further, reconstruction device 114 can execute pre-reconstruction processing and image processing, such as volume rendering processing and image difference processing, as needed.

The pre-reconstruction processing of the projection data performed by the preprocessing device 106 can include correcting for detector calibrations, detector nonlinearities, polar effects, noise balancing, and material decomposition.

Post-reconstruction processing performed by the reconstruction device 114 can include filtering and smoothing the image, volume rendering processing, and image difference processing as needed. The image reconstruction process can be performed using filtered back projection, iterative image reconstruction methods, or stochastic image reconstruction methods. The reconstruction device 114 can use the memory to store, e.g., projection data, reconstructed images, calibration data and parameters, and computer programs.

The reconstruction device 114 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 112 can be non-volatile, such as ROM, EPROM, EEPROM or FLASH memory. The memory 112 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 114 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 116. The display 116 can be an LCD display, CRT display, plasma display, OLED, LED, or any other display known in the art.

The memory 112 can be a hard disk drive, CD-ROM drive, DVD drive, FLASH drive, RAM, ROM, or any other electronic storage known in the art.

After obtaining CT projection data, the CT imaging system using the reconstruction device 114 will perform image reconstruction using the projection data. Conventional approaches to image reconstruction include filtered back projection (FBP), iterative reconstruction methods (e.g., the algebraic reconstruction technique (ART) method and the total variation minimization regularization method), Fourier-transform-based methods (e.g., the direct Fourier method), and statistical methods (e.g., maximum-likelihood expectation-maximization algorithm based methods).

Figure 2:
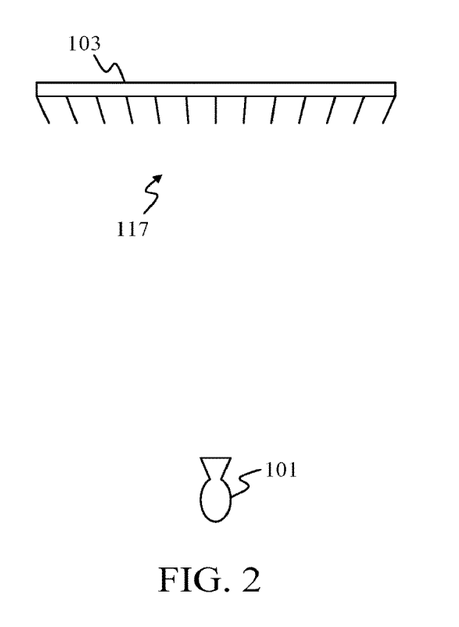
FIG. 2 illustrates a disposition of an anti-scatter grid on an X-ray detector in an exemplary aspect of the disclosure.

FIG. 2 shows the X-ray tube 101 facing the X-ray detector 103. Anti-scatter grid 117 is disposed on a surface of the X-ray detector 103. The anti-scatter grid 117 includes walls, or septa, which project from the X-ray detector toward the X-ray source. The anti-scatter grid 117 acts as a collimator to filter, or limit, scattered radiation which would otherwise be incident on the detector plane, but which is not incident in a direction from the X-ray source.

Figure 3A:
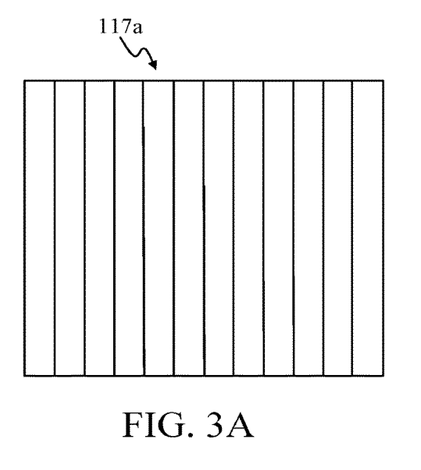
FIG. 3A illustrates a first cross-section of an anti-scatter grid in an exemplary aspect of the disclosure.
Figure 3B:
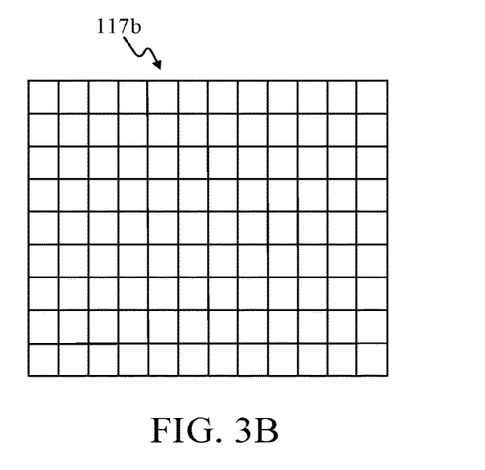
FIG. 3B illustrates a second cross-section of an anti-scatter grid in an exemplary aspect of the disclosure.

The walls of the anti-scatter grid can be disposed, for example, in a series of columns, called a one-dimensional grid 117a, as shown in FIG. 3A (shown from the point of view of the X-ray tube 101). The walls of the anti-scatter grid can also be disposed, for example, in a series of columns and rows, called a two-dimensional grid 117b, as shown in FIG. 3B (also shown from the point of view of the X-ray tube 101). The cells defined by the walls of the two-dimensional grid 117b may have a square or rectangular cross-section, for example.

Figure 4:
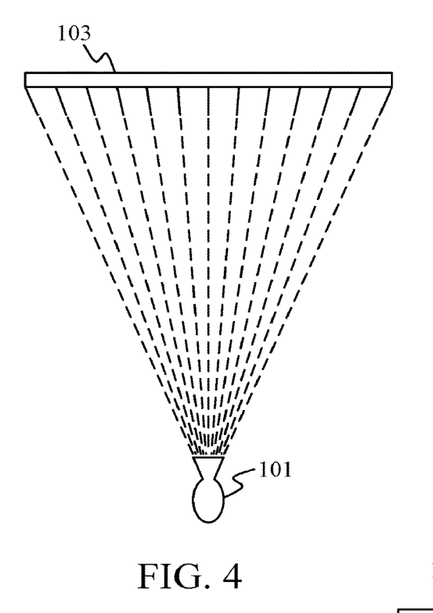
FIG. 4 illustrates a flat field or uniform illumination of an X-ray detector and anti-scatter grid in an exemplary aspect of the disclosure.

Being between the X-ray tube 101 and the X-ray detector 103, the anti-scatter grid 117 will appear in projection data along with the intended target. The conventional technique to remove the anti-scatter grid 117 from the projection data uses a combination of dark images, which are images taken while the X-ray detector 103 is not illuminated, and flat-field images, which are images taken without a target and with uniform illumination by the X-ray tube 101 on the X-ray detector 103, as shown in FIG. 4, to correct the two-dimensional projection data for the presence of the anti-scatter grid 117. The dark images are used to remove the effect of dark currents in the detector, and the flat-field images are used to correct for photo response non-uniformity in the detector and to correct for the presence of the anti-scatter grid. This procedure corrects the grid pattern due to the primary X-ray beam.

Figure 5:
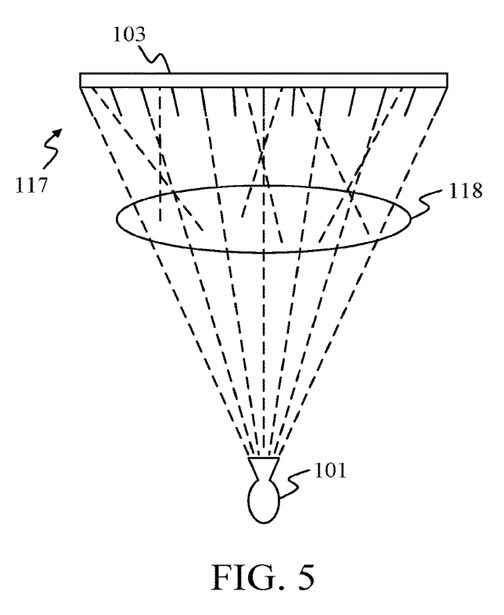
FIG. 5 illustrates a flat field or uniform illumination of an X-ray detector and anti-scatter grid with scatter due to an object in the field of view in an exemplary aspect of the disclosure.

However, as shown in FIG. 5, the presence of an object 118 generates additional scattering which is not present in the flat-field image, even for an object having uniform density. This scattered X-ray beam causes a residual grid pattern in the projection data, which is not removed by the procedure for correcting the grid pattern in the primary X-ray beam.

Figure 6:
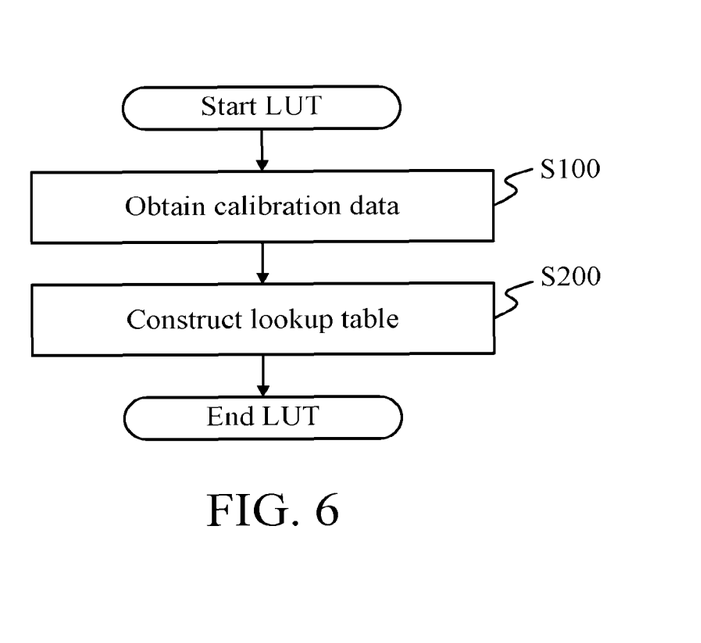
FIG. 6 illustrates an algorithm for constructing a lookup table for estimating grid pattern due to scatter in an exemplary aspect of the disclosure.

In FIG. 6, a method for constructing a lookup table for estimating the error due to the grid pattern from scattered radiation and correcting the projection data according to the present disclosure begins at step S100 by capturing calibration data for creating the lookup table. The lookup table entries are parametrized by a set of values that correspond to controllable factors that influence scatter. The lookup table can be parametrized, for example, by a set of parameters including peak kilovoltage, field size, patient-detector distance, and size of the DC scatter component. Calibration data is captured for every combination of parameter values for which it is desired to correct projection data.

At step S200, the lookup table is constructed based on the calibration data. The entries in the lookup table facilitate the correction of reconstructed images, and are indexed according to the same parameter values for which the calibration data is captured. The lookup table can be stored, for example, in memory 112. The lookup table entries can be quickly accessed based on the values of the parameters in the lookup table in order to provide a correction of the grid pattern due to scatter, without having to perform complicated calculations. The lookup table entries include the scatter values, or Fourier components, of the projection data for each combination of parameter values in the lookup table, and for each scatter DC value in the lookup table.

This completes the method for constructing a lookup table for estimating the error due to the grid pattern from scattered radiation and correcting the projection data.

Figure 7:
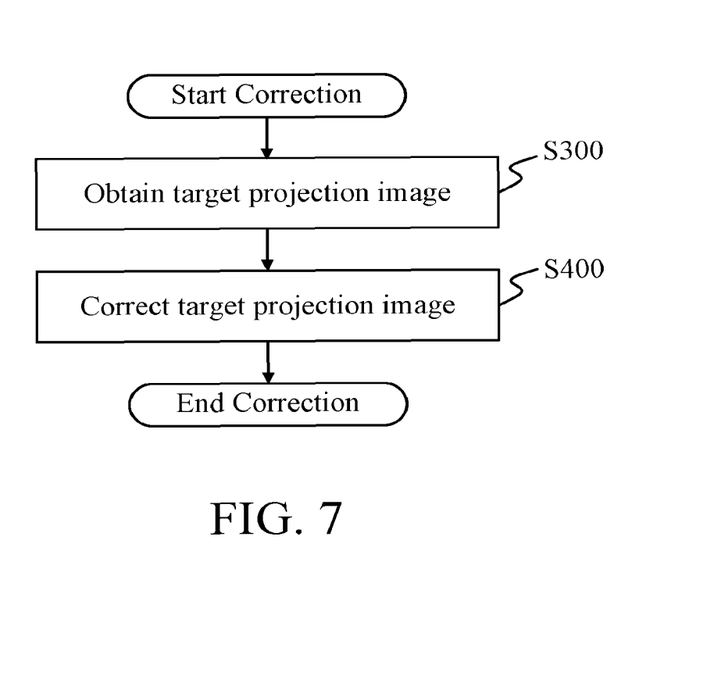
FIG. 7 illustrates an algorithm for using a lookup table for correcting grid pattern due to scatter in an exemplary aspect of the disclosure.

FIG. 7 illustrates an algorithm for using the lookup table for correcting for the grid pattern due to scatter in an exemplary aspect of the disclosure.

At step S300, projection data of a target is obtained. Here, "projection data" means the values measured by the X-ray detector 103, or the Fourier transform of the data in the frequency domain, since the discussion here focuses primarily on scatter correction. Since the data being transformed is spatial projection data, frequency indicates spatial frequency and not temporal frequency.

At step S400, the projection data is corrected using the data from the lookup table. The correction terms in the lookup table correspond to frequency domain data, and the projection data is corrected after Fourier transformation into the frequency domain.

The lookup table can be parametrized, for example, by a set of parameters including peak kilovoltage, field size, patient-detector distance, and size of the DC scatter component. The peak kilovoltage, field size, and patient-detector distance are determined or measured parameters. The size of the DC scatter component is determined from the Fourier transform of the projection data. Using the parameter values, the AC scatter values, or scatter values, for the spatial frequency components are given by the lookup table entries. The scatter values are subtracted from the projection data values for each respective frequency to correct the projection data. The projection data correction may be performed, for example, by the preprocessing device 106.

Figure 8:
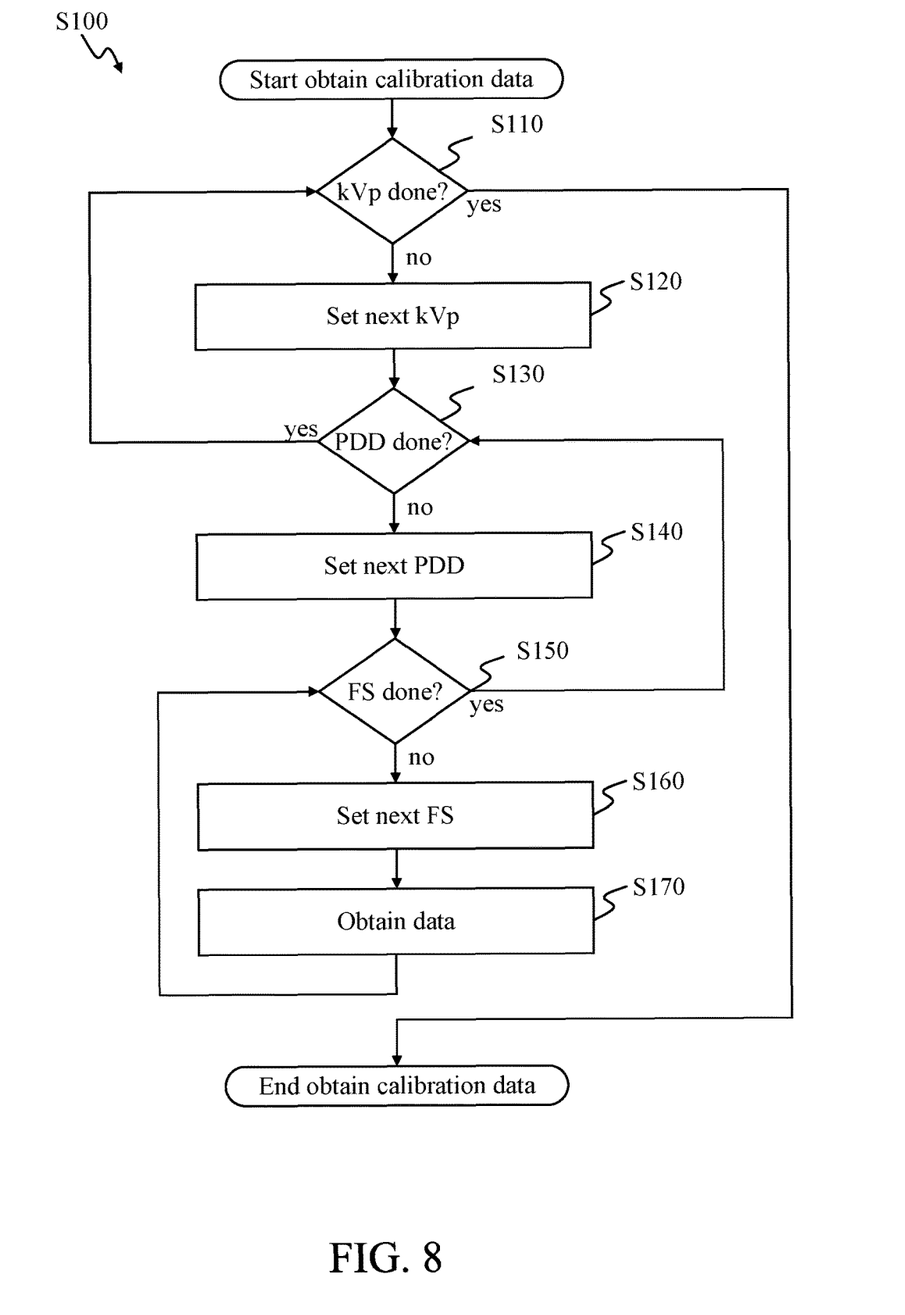
FIG. 8 illustrates an algorithm for obtaining calibration data in an exemplary aspect of the disclosure.

This completes the algorithm for using the lookup table for correcting grid pattern due to scatter in an exemplary aspect of the disclosure In FIG. 8, an exemplary process for performing step S100 (obtaining calibration data) according to the present disclosure begins at step S110 with determining whether data has been obtained for all the desired peak kilovoltage (kVp) values. The peak kilovoltage is the maximum voltage applied across the X-ray tube 101. The peak kilovoltage determines the peak energy of the X-ray emission spectrum. If data has been obtained for all the desired kVp values, then the process is complete and ends. If data has not been obtained for all the desired kVp values, then the process continues to step S120.

At step S120, the X-ray tube 101 is set to the next kVp value for collection of calibration data.

At step S130, it is determined whether data has been obtained for all the desired patient-detector distances (PDD). A PDD is a distance from the intended target of a projection to the X-ray detector 103. If data has been obtained for all the desired PDD values, then the process returns to step S110. If data has not been obtained for all the desired PDD values, then the process continues to step S140.

At step S140, the PDD is set to the next value for collection of calibration data. For obtaining calibration data, a uniform phantom is placed at the next PDD, which is the next in a set of predetermined positions. A phantom is a designed object that is scanned or imaged to evaluate and analyze the performance of an imaging device. A uniform phantom is a phantom constructed of a material so as to be uniform in density. The choice of the phantom thickness will depend on the application. Usually 6-inch Poly(methyl methacrylate) (PMMA) is used to mimic the human head while an 8-inch PMMA is used for torso applications. The phantom material need not be PMMA; any material with a density similar to human tissue can be used as a phantom material.

Figure 9:
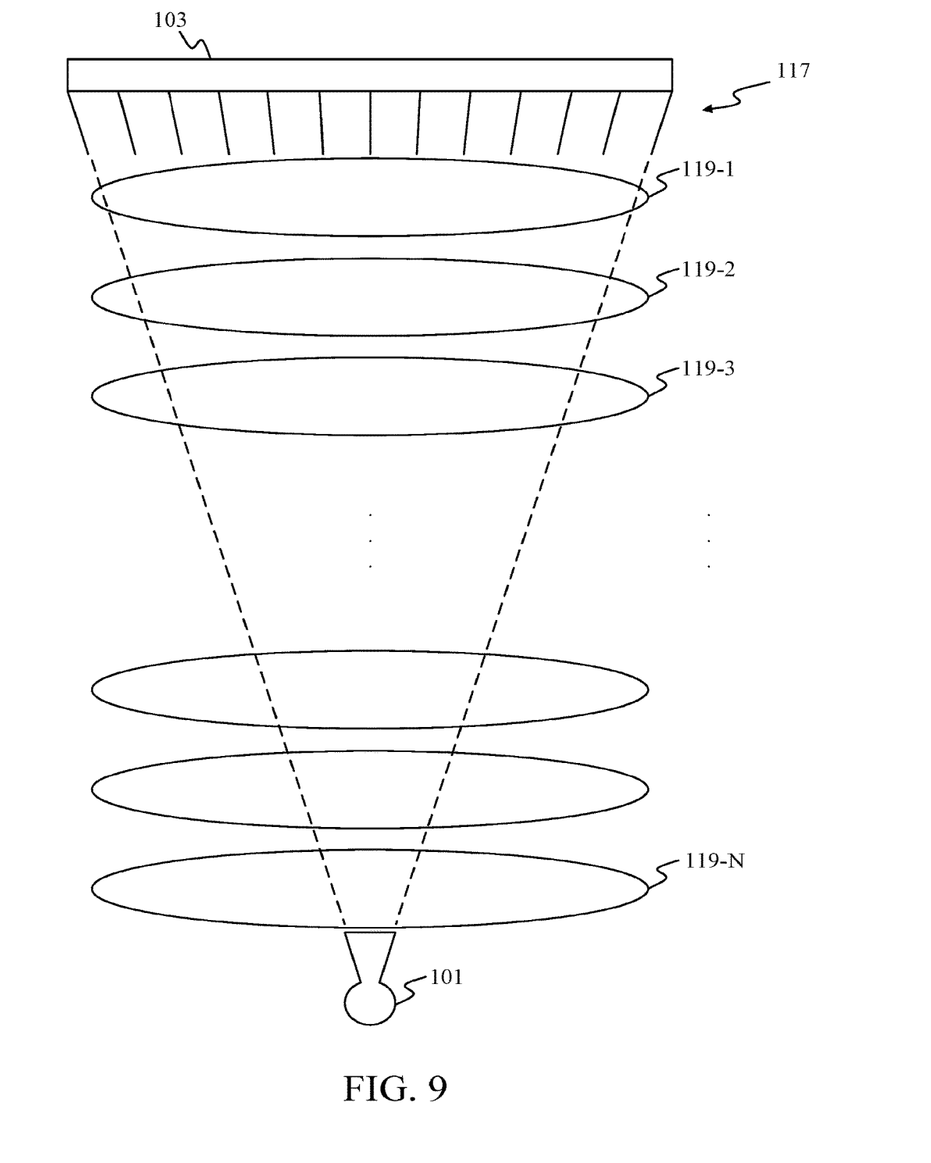
FIG. 9 illustrates a series of positions of a uniform phantom in an exemplary aspect of the disclosure.

During the process of obtaining calibration data, the uniform phantom is imaged at a set of positions 119-1 through 119-N between the X-ray tube 101 and the X-ray detector 103, as shown in FIG. 9. The first position 119-1 is adjacent to the anti-scatter grid 117 and the last position 119-N is adjacent to X-ray tube 101. The number of positions N is not fixed, but more positions will allow a more accurate correction of projection data. For example, 8 positions can be used.

At step S150, it is determined whether data has been obtained for all the desired field sizes (FS). A field size gives the dimensions of the treatment field, for example, 5 cm by 5 cm, 20 cm by 20 cm, 20 cm by 40 cm, etc. A series of projections will be obtained at each position in the series (i.e., at each PDD) for a variety of different desired field sizes. The different field sizes can be measured or interpolation can be used to estimate a field size. In another embodiment, the field size is estimated based on the field-of-view, the source-to-detector distance, and the patient-to-detector distance. The set of field sizes can be chosen, for example, as a set of the common field sizes which occur when imaging a typical human, e.g., a size for a head, a size for a heart, etc. If data has been taken for all the desired FS values, then the process returns to step S130. If data has not been taken for all the desired PDD values, then the process continues to step S160.

At step S160, the next FS value is selected. The field size is controlled by an amount of collimation in the X-ray tube 101, that is, by reducing the aperture on the X-ray tube, using metal leaves or plates, for example.

At step S170, projection data is obtained of the uniform phantom for the current kVp, PDD, and FS values. Multiple projections may be taken for each field size and averaged to reduce the noise, for example 10 or 100 projections can be averaged. The result of this step is a calibration projection corresponding to the current kVp, PDD, and FS values. After acquiring the projection data, the process returns to step S150.

The process to obtain calibration data ends when projection data has been acquired and a calibration projection formed for all combinations of desired kVp, PDD, and FS values.

Figure 10:
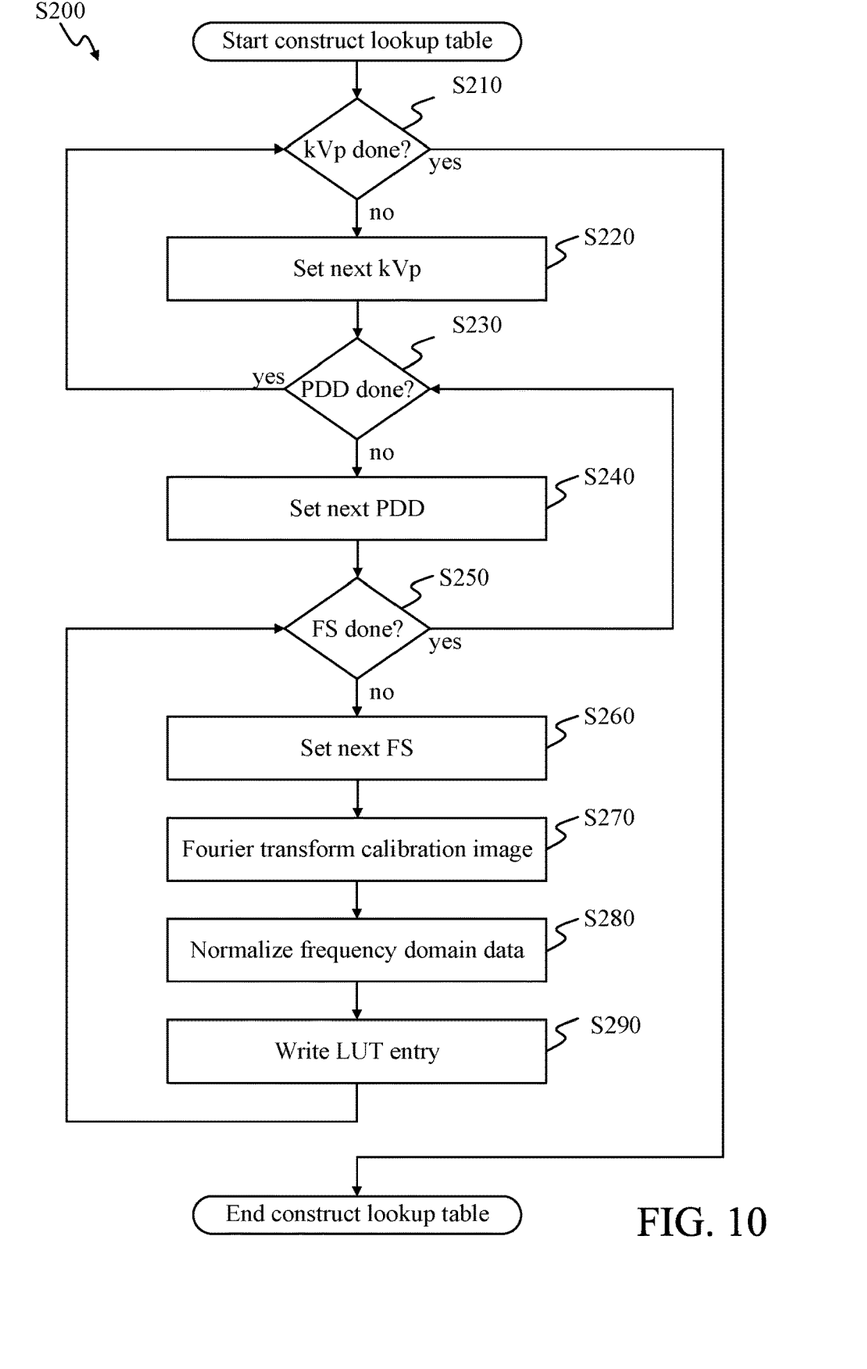
FIG. 10 illustrates an algorithm for constructing a lookup table in an exemplary aspect of the disclosure.

In FIG. 10, an exemplary process for performing step S200 (constructing a lookup table) according to the present disclosure begins at step S210 by determining whether the lookup table entries have been calculated for all the desired peak kilovoltage (kVp) values. If lookup table entries have been calculated for all the desired kVp values, then the process is complete and ends. If lookup table entries have not been calculated for all the desired kVp values, then the process continues to step S220.

At step S220, the process moves to the next kVp value for which to calculate the lookup table values.

At step S230, it is determined whether lookup table entries have been calculated for all the desired patient-detector distances (PDD). If lookup table entries have been calculated for all the desired PDD values, then the process returns to step S210 If lookup table entries have not been calculated for all the desired PDD values, then the process continues to step S240.

At step S240, the process moves to the next PDD value for which to calculate the lookup table values.

At step S250, it is determined whether lookup table entries have been calculated for all the desired field size (FS) values. If lookup table entries have been calculated for all the desired FS values, then the process returns to step S230. If lookup table entries have not been calculated for all the desired FS values, then the process continues to step S260.

At step S260, the process moves to the next FS value for which to calculate the lookup table values.

At step S270 of the process, the calibration projection corresponding to the current values of kVp, PDD, and FS is Fourier transformed into the frequency domain. This may be done, for example, using a fast Fourier transform (FFT).

At step S280, the Fourier components of the calibration projection are normalized by dividing each Fourier component by the corresponding Fourier component from the position closest to the X-ray tube 101, that is, from the position 119-N.

At step S290, the normalized Fourier components are stored in a lookup table for later use in projection data correction, indexed by the kVp, PDD, and FS values. Since the phantom used to capture the data is uniform, the normalized AC Fourier components, i.e., the variation from a flat field, are due to the presence of the anti-scatter grid and scatter caused by the uniform phantom, and the normalized Fourier components form the basis for estimation and correction of grid pattern due to scatter.

The process to construct the lookup table ends when normalized frequency domain data has been calculated and lookup table values populated for all desired combinations of kVp, PDD, and FS values.

Figure 11:
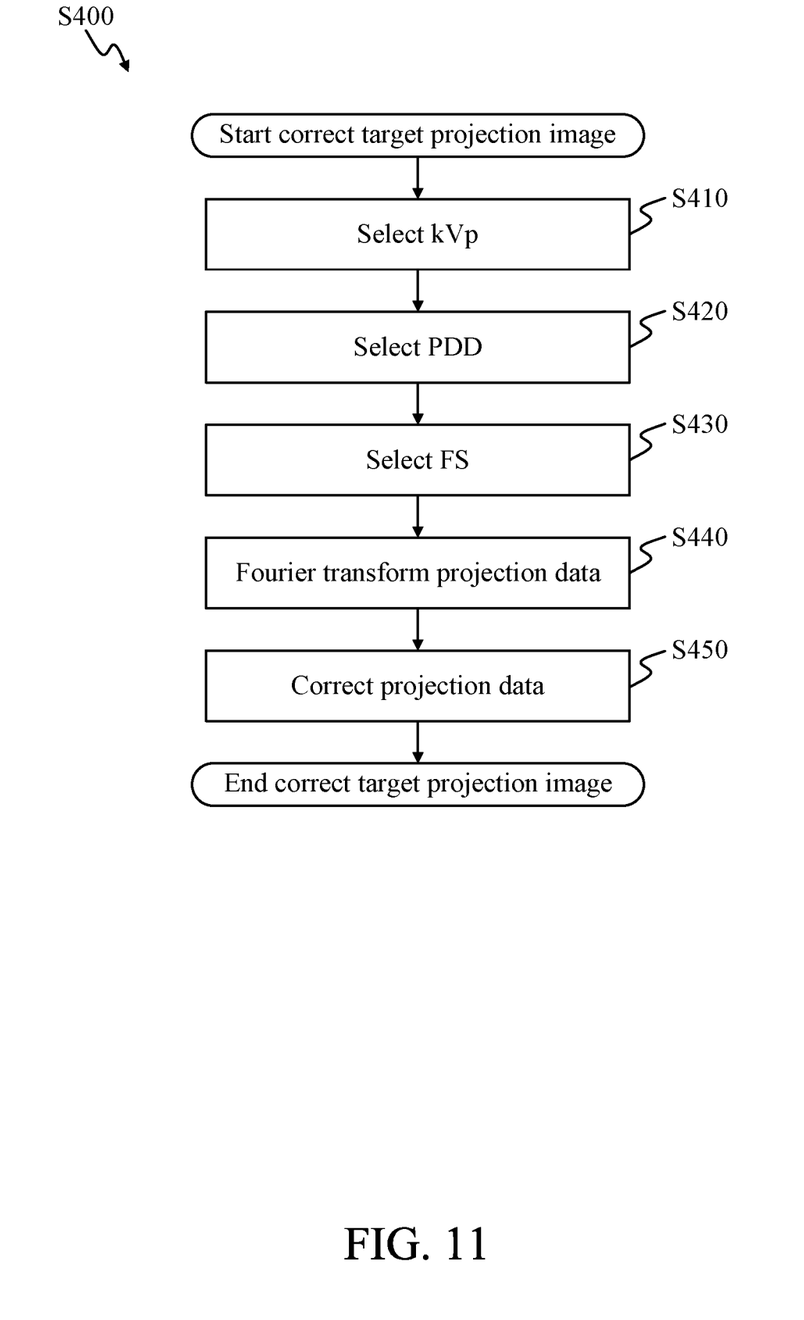
FIG. 11 illustrates an algorithm for correcting a target projection image in an exemplary aspect of the disclosure.

In FIG. 11, an exemplary process for performing step S400 (correcting target projection data) according to the present disclosure begins at step S410 by determining the peak kilovoltage (kVp) used in acquiring the target projection data. At step S420 of the process, the patient-detector distance (PDD) used in acquiring the target projection data is determined. The field size (FS) is determined at step S430.

At step S440, the target projection data is Fourier transformed into the frequency domain. This may be done, for example, using a fast Fourier transform (FFT). The result of the Fourier transform of the projection data are DC and AC frequency components corresponding to the projection data, for example, 1 DC component and k AC components.

The measured scatter fraction for a given combination of kVp, FS, and PDD is normalized. Thus, the DC component of scatter fraction will range between 0 to 1. The actual values of scatter present are calculated with intensity of the image and scatter fraction value from the look-up table. Then, based on the actual values of the scatter, the spatial frequency component magnitude is calculated.

Figure 12:
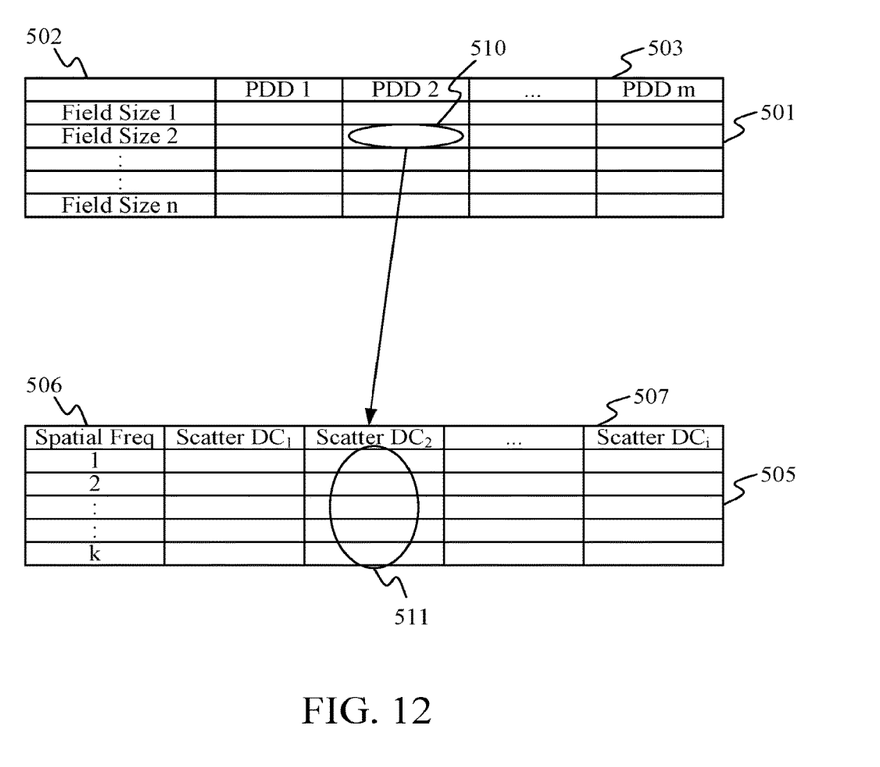
FIG. 12 illustrates a structure of a lookup table for a particular kVp value in an exemplary aspect of the disclosure.

At step S450, the projection data is corrected. The projection data is corrected using scatter values determined from the lookup table. FIG. 12 illustrates a structure of the lookup table for a particular kVp value in an exemplary aspect of the disclosure.

For a given kVp value, which is a first parameter determined at step S410, the lookup table has the values of the field size (FS) as a second parameter 502 determined at step S430. The values of the patient-detector distance, or PDD, are a third parameter 503 determined at step S420. The scatter DC value is determined as the magnitude of the DC component of the projection data. The scatter DC values are a fourth parameter 507.

The appropriate field size parameter value and PDD parameter value for the projection data are used to determine a location 510 in a first lookup table 501. The value of the scatter DC parameter at the location 510 is used to identify a column of spatial frequency scatter values 511 corresponding to the scatter DC value in a second lookup table 505. The scatter values for the spatial frequencies 1, 2, ..., k 506 are subtracted from the corresponding AC components of the projection data.

This completes the exemplary process for performing step S400 (correcting target projection data) according to the present disclosure.

In another embodiment, since scatter depends on the thickness of a phantom, a plurality of look-up-tables (LUTs) are generated for different thicknesses of phantoms. The LUT generating procedure described above is used repeatedly to generate the plurality of LUTs for the different thicknesses. Then, based on the thickness of the patient, a specific LUT of the plurality of LUTs is chosen. For example, for a cardiac scan, where the thickness of a patient can vary significantly, a thickness-dependent LUT is useful, and an appropriate LUT can be chosen.

In other embodiments, the correction can be performed in volume data domain. In one embodiment, each projection is corrected based on the scatter fraction estimated, based on the thickness, kVp, PDD and FS information. Another embodiment involves data reconstruction, and includes the following steps: (1) perform reconstruction using the projection data, which will result in exact information of the attenuation and thickness of the object, (2) forward project the reconstructed data, wherein for each forward projection, scatter will be calculated based on the thickness and location of the object, and (3) use the calculated scatter fraction to correct the projection data and then perform reconstruction again on the corrected data.

While certain embodiments have been described herein, these embodiments are presented by way of example only, and are not intended to limit the scope of the disclosure. Indeed, using the teachings in this disclosure, a person having ordinary skill in the art could modify and adapt the disclosure in a various ways, making omissions, substitutions and changes in the form of the embodiments described herein without departing from the spirit of the disclosure. Moreover, in interpreting the disclosure, all terms should be interpreted in the broadest possible manner consistent with the context. The accompanying claims and their equivalents are intended to cover such forms or modifications as would fall within the scope and spirit of the disclosure.

For example, while the method is illustrated using a conventional CT machine, the method is applicable in any situation which uses an anti-scatter grid over a detector, including not only conventional CT, but conventional X-ray, single-photon emission CT (SPECT), positron emission tomography (PET), fluoroscopy, angiography, and the like, and is applicable whether the anti-scatter grid and detector are one- or two-dimensional.

Also, an order of adjusting parameters such as kVp, PDD, and FS is given for obtaining calibration data for a lookup table, but the particular order in which data is obtained to calculate the calibration data may vary. It is not important in what way the parameters are varied to obtain the calibration data to produce the lookup table, but only that the lookup table is populated for any values for which actual target projection data will be acquired and corrected.

While the series of projections was averaged to produce a calibration projection for each value of kVp, PDD, and FS in the process of obtaining calibration data, the series of projections could also be recorded during the process of obtaining calibration data. In such a case, the averaging could then be performed, for example, in the process of constructing the lookup table.

The invention claimed is:

1. A method of calibrating a pattern of an anti-scatter grid induced by X-ray scatter on a detector array of an X-ray imager, the method comprising:
   obtaining a first calibration image and a second calibration image, each calibration image being a projection image in which a uniform phantom is fixed at a respective position between the detector array and an X-ray source of the X-ray imager, the position of the uniform phantom being spaced from the detector array by a respective patient-to-detector distance (PDD), which is different for the first projection image and the second projection image, respectively, the PDD of the first projection image corresponding to a position at which an object to be imaged is to be arranged during X-ray imaging using the X-ray imager,
   generating a ratio image between the first calibration image and a second calibration image, and using the ratio image to estimate a background-scatter image due to scatter,
   performing a spatial-frequency transformation on the background-scatter image, and
   storing, as a calibration result, in a memory (i) non-zero frequency components of the spatial-frequency transformation as a zero-mean scatter pattern, and (ii) a zero frequency component of the spatial-frequency transformation as a scaling factor.

2. The method according to claim 1, wherein the generating of the ratio image further includes calculating the ratio image by dividing respective pixels of the first calibration image by corresponding pixels of the second calibration image.

3. The method according to claim 2, wherein
   the obtaining of the second calibration image further includes that the PDD of the second projection image is such that the uniform phantom is adjacent to the X-ray source, and
   the estimate of the background-scatter image is performed by using the ratio image as the background-scatter image.

4. The method according to claim 1, further comprising determining, for various configurations of the X-ray imager, a plurality of combinations of X-ray imaging parameters, which are to be calibrated, the X-ray imaging parameters including a plurality of PDD values corresponding to respective first calibration images, each of the PDD values representing a distance from the X-ray detector at which the objected to be imaged can be arranged during the acquisition of projection data representing a series of one or more projection images acquired at one or more projection angles,
   obtaining respective first calibration images for each of the combinations of X-ray imaging parameters, and
   preforming, for each of the combinations of X-ray imaging parameters, the steps of:
      generating the ratio image and estimating the background-scatter image,
      performing the spatial-frequency transformation on the background-scatter image, and
      storing, as respective calibration results, the zero-mean scatter pattern and the scaling factor, wherein
   the stored zero-mean scatter patterns and the stored scaling factors comprise a lookup table of respective calibration results indexed according to the combinations of X-ray imaging parameters.

5. The method according to claim 4, wherein the determining of the plurality of combinations of the X-ray imaging parameters further includes that the X-ray imaging parameters include
- a plurality of peak kilovoltage (kVp) values, each of the kVp values representing a voltage to be applied to the X-ray source during respective acquisitions of the projection data, and
- a plurality of field size (FS) values, each of the FS values representing a size of a field of view of an X-ray beam from the X-ray source to be used during the respective acquisitions of the projection data.

6. The method according to claim 1, further comprising repeating, for a series of projection angles in which the uniform phantom remains fixed in space and the X-ray source rotates through the series of projection angles, the steps of
- obtaining respective first calibration images and respective second calibration images corresponding to the series of projection angles,
- generating respective ratio images and estimating respective background-scatter images corresponding to the series of projection angles, and
- generate respective scaling factors corresponding a zero frequency component of the spatial-frequency transformation of the respective background-scatter images and respective zero-mean scatter patterns that correspond to the series of projection angles,
- reconstructing a computed tomography (CT) calibration image using the zero-mean scatter patterns and storing the CT calibration image together with the scaling factors in the memory, and
- storing, as another calibration result, in the memory the CT calibration image and the scaling factors.

7. The method according to claim 4, wherein the stored zero-mean scatter patterns and the stored scaling factors further comprise the lookup table of respective calibration results indexed according the stored scaling factors.

8. The method according to claim 1, wherein for respective combinations of the plurality of combinations of the X-ray imaging parameters two or calibration results are generated, each of the two or more calibration results being generated using one of two or more uniform phantoms, each of the two or more uniform phantoms having a different thickness and/or X-ray attenuation density representing a different part of a patient's body.

9. A method of correcting uniform background scatter in X-ray projection data acquired using an X-ray imager having an anti-scatter-grid, the method comprising:
- reading the calibration result of claim 1 from the memory, including the zero-mean scatter pattern and the scaling factor;
- obtaining a projection image of the object to be imaged that was acquired using the X-ray imager when the object to be imaged was arranged at a position corresponding to the PDD of the first calibration image;
- modifying the zero-mean scatter based on the scaling factor and an average X-ray intensity represented by the projection image; and
- subtracting from the projection image a product of the modified zero-mean scatter.

10. A method of correcting uniform background scatter in X-ray projection data acquired using an X-ray imager having an anti-scatter-grid, the method comprising:
- reading the another calibration result of claim 6 from the memory, including the CT image and the scaling factors;
- obtaining a projection scan of the object to be imaged that was acquired using the X-ray imager to acquire a series of object projection images at the series of projection angles when the object to be imaged was arranged at a position corresponding to the PDD used to generate the CT calibration image;
- generating a modified scaling factor based on the scaling factors and an average X-ray intensity represented by the projection scan;
- reconstructing a CT image using the projection scan; and
- subtracting from the CT image a product of the CT calibration image and the modified scaling factor.

11. A method of correcting uniform background scatter in X-ray projection data acquired using an X-ray imager having an anti-scatter-grid, the method comprising:
- obtaining a projection image of an object, the projection image being acquired using one combination of a plurality of combinations of the X-ray imaging parameters;
- reading, from the lookup table of claim 4 stored in the memory, a calibration result corresponding to the one combination of the X-ray imaging parameters, the calibration result including a zero-mean scatter pattern and a scaling factor generated using the one combination of the X-ray imaging parameters;
- modifying the scaling factor based on an average X-ray intensity represented by the projection image; and
- subtracting from the projection image a product of the zero-mean scatter and the modified scaling factor.

12. A method of correcting uniform background scatter in X-ray projection data acquired using an X-ray imager having an anti-scatter-grid, the method comprising:
- obtaining a projection image of an object, the projection image being acquired using one combination of a plurality of combinations of the X-ray imaging parameters;
- reading, from the lookup table of claim 7 stored in the memory, a calibration result corresponding to the one combination of the X-ray imaging parameters, the read calibration result including the zero-mean scatter pattern and the scaling factor corresponding to the one combination of the X-ray imaging parameters, and the read calibration result being selected from among all calibration results corresponding to the one combination of the X-ray imaging parameters to have a value of the scaling factor that most closely matches an average X-ray intensity of the projection image,
- modifying the zero-mean scatter based on the scaling factor of the read calibration result and based on the average X-ray intensity of the projection image; and
- subtracting from the projection image a product of the modified zero-mean scatter.

13. A non-transitory computer readable storage medium including executable instruction, wherein the instructions, when executed by circuitry, cause the circuitry to perform the method according to claim 1.

14. An X-ray imager that calibrates a pattern of an anti-scatter grid induced by X-ray scatter, the X-ray imager comprising:
- an imaging system including
  - an X-ray source, and
  - a detector array arranged across from the X-ray source, and acquire projection images representing an intensity of X-ray radiation detected by the detector array, the projections images acquired by the detector array including a first calibration image and a second calibration image, wherein each of the first calibration image and second calibration image is a projection image in which a uniform phantom is fixed at a respective position between the detector array and an X-ray source of the X-ray imager, the position of the uniform phantom being spaced from the detector array by a respective patient-to-detector distance (PDD), which is different for the first projection image and the second projection image, respectively, the PDD of the first projection image corresponding to a position at which an object to be imaged is to be arranged during X-ray imaging using the X-ray imager; and circuitry configured to
 generate a ratio image between the first calibration image and a second calibration image, and using the ratio image to estimate a background-scatter image due to scatter,
 perform a spatial-frequency transformation on the background-scatter image, and
 store, as a calibration result, in a memory (i) non-zero frequency components of the spatial-frequency transformation as a zero-mean scatter pattern, and (ii) a zero frequency component of the spatial-frequency transformation as a scaling factor.

15. The X-ray imager to claim 14, wherein the circuitry is further configured to generate of the ratio image by calculating the ratio image by dividing respective pixels of the first calibration image by corresponding pixels of the second calibration image.

16. The X-ray imager according claim 15, wherein
 the imaging system is further configured to obtain the second calibration image such that the PDD of the second projection image is such that the uniform phantom is adjacent to the X-ray source, and
 the circuitry is further configured to generate of the ratio image by estimating the background-scatter image using the ratio image as the background-scatter image.

17. The X-ray imager according to claim 14, wherein the circuitry is further configured to
 determine, for various configurations of the X-ray imager, a plurality of combinations of X-ray imaging parameters, which are to be calibrated, the X-ray imaging parameters including a plurality of PDD values corresponding to respective first calibration images, each of the PDD values representing a distance from the X-ray detector at which the objected to be imaged can be arranged during the acquisition of projection data representing a series of one or more projection images acquired at one or more projection angles,
 obtain respective first calibration images for each of the combinations of X-ray imaging parameters, and
 preform, for each of the combinations of X-ray imaging parameters, the steps of:
  generating the ratio image and estimating the background-scatter image,
  performing the spatial-frequency transformation on the background-scatter image, and
  storing, as respective calibration results, the zero-mean scatter pattern and the scaling factor, wherein
 the stored zero-mean scatter patterns and the stored scaling factors comprise a lookup table of respective calibration results indexed according to the combinations of X-ray imaging parameters.

18. The X-ray imager according to claim 17, wherein the circuitry is further configured to determine the plurality of combinations of the X-ray imaging parameters further, wherein the X-ray imaging parameters include
 a plurality of peak kilovoltage (kVp) values, each of the kVp values representing a voltage to be applied to the X-ray source during respective acquisitions of the projection data, and
 a plurality of field size (FS) values, each of the FS values representing a size of a field of view of an X-ray beam from the X-ray source to be used during the respective acquisitions of the projection data.

19. The X-ray imager according to claim 14, wherein the circuitry is further configured to
 repeat, for a series of projection angles in which the uniform phantom remains fixed in space and the X-ray source rotates through the series of projection angles, the steps of
  obtaining respective first calibration images and respective second calibration images corresponding to the series of projection angles,
  generating respective ratio images and estimating respective background-scatter images corresponding to the series of projection angles, and
  generate respective scaling factors corresponding a zero frequency component of the spatial-frequency transformation of the respective background-scatter images and respective zero-mean scatter patterns that correspond to the series of projection angles,
 reconstructing a computed tomography (CT) calibration image using the zero-mean scatter patterns and storing the CT calibration image together with the scaling factors in the memory, and
 storing, as another calibration result, in the memory the CT calibration image and the scaling factors.

20. The X-ray imager according to claim 14, wherein the circuitry is further configured to
 read the calibration result from the memory, including the zero-mean scatter pattern and the scaling factor,
 obtain a projection image of the object to be imaged that was acquired using the X-ray imager when the object to be imaged was arranged at a position corresponding to the PDD of the first calibration image,
 modify the zero-mean scatter based on the scaling factor and an average X-ray intensity represented by the projection image, and
 subtract from the projection image a product of the modified zero-mean scatter.

* * * * *